(12) United States Patent
Sato et al.

(10) Patent No.: US 7,381,833 B2
(45) Date of Patent: Jun. 3, 2008

(54) PROCESS FOR PRODUCING 1,2-CIS-2-FLUOROCYCLOPROPANE-1-CARBOXYLIC ESTER COMPOUND

(75) Inventors: Koji Sato, Edogawa-ku (JP); Makoto Imai, Edogawa-ku (JP)

(73) Assignee: Daiichi Pharmaceutical Co., Ltd., Tokyo (JP)

(*) Notice: Subject to any disclaimer, the term of this patent is extended or adjusted under 35 U.S.C. 154(b) by 0 days.

(21) Appl. No.: 10/593,420

(22) PCT Filed: Mar. 31, 2005

(86) PCT No.: PCT/JP2005/006240

§ 371 (c)(1),
(2), (4) Date: Sep. 19, 2006

(87) PCT Pub. No.: WO2005/095322

PCT Pub. Date: Oct. 13, 2005

(65) Prior Publication Data

US 2007/0191626 A1    Aug. 16, 2007

(30) Foreign Application Priority Data

Mar. 31, 2004  (JP)  .............................. 2004-102746

(51) Int. Cl.
*C07C 69/74* (2006.01)

(52) U.S. Cl. ...................................................... 560/124
(58) Field of Classification Search ..................... None
See application file for complete search history.

(56) References Cited

U.S. PATENT DOCUMENTS 5,780,669 A    7/1998    Akiba et al.
2006/0052626 A1    3/2006    Tani et al.

FOREIGN PATENT DOCUMENTS

| JP | 06 065140 | | 3/1994 |
| JP | 06 157418 | | 6/1994 |
| JP | 06-157418 | * | 6/1994 |
| WO | 95 04712 | | 2/1995 |
| WO | 2004 060851 | | 7/2004 |

OTHER PUBLICATIONS

Hutchins et al, Journal of Organic Chemistry, Nucleophilic Borohydride: Selective Reductive Displacement of Halides, Sulfonate Esters, Tertiary Amines and N, N-Disulfonimides with Borohydride Reagents in Polar Aprotic Solvents, 1978, 43(11), p. 2259-2267.*

U.S. Appl. No. 10/593,420, filed Sep. 19, 2006, Sato et al.

* cited by examiner

*Primary Examiner*—Paul A Zucker
(74) *Attorney, Agent, or Firm*—Oblon, Spivak, McClelland, Maier & Neustadt, P.C.

(57) ABSTRACT

The present invention provides a for producing 1,2-cis-2-fluorocyclopropane-1-carboxylic ester.

26 Claims, No Drawings

PROCESS FOR PRODUCING 1,2-CIS-2-FLUOROCYCLOPROPANE-1-CARBOXYLIC ESTER COMPOUND

TECHNICAL FIELD

The present invention relates to a process for producing a fluorocyclopropane compound that is useful as an intermediate for the production of a quinolone compound serving as an excellent medicine or agrochemical.

BACKGROUND ART

Among the new quinolone synthetic antibacterial agents, those having a 1,2-cis-2-fluorocyclopropyl group as a 1-position substituent exhibit strong antibacterial activity and high safety, and therefore are expected to serve as excellent synthetic antibacterial agents. A raw material necessary to obtain a 1,2-cis-2-fluorocyclopropyl group is prepared by use of 1,2-cis-2-fluorocyclopropane-1-carboxylic acid. This compound is synthesized by dechlorination of 1-chloro-2-fluorocyclopropane-1-carboxylic ester in dimethyl sulfoxide in the presence of sodium borohydride (see Patent Document 1).

However, such dechlorination turned out to be so problematic that when a reaction is conducted under stirring by a stirring blade under the industrial-scale, the viscosity of a reaction mixture sharply increases as the reaction proceeds and thereby weakens the stirring efficiency, and the reaction rate slows down as a result, so that a long period of time (several days) is required until the completion of said reaction. Furthermore, such dechlorination turned out to cause another problem in that when conducted by use of dimethyl sulfoxide serving as a solvent, the reaction produces dimethyl sulfide as a by-product having offensive odor and thus ends up with the worsening of working environment.

Patent Document 1: JP-A-1994-157418

DISCLOSURE OF THE INVENTION

Problems to be Solved by the Invention

Accordingly, an object of the present invention is to provide an industrially applicable process for producing 1,2-cis-2-fluorocyclopropane-1-carboxylic ester.

Means for Solving the Problems

In view of the foregoing, the present inventors conducted extensive studies thereon. As a result, it has been found that when a 2-fluorocyclopropane-1-carboxylic ester having, at position 1 or 2, a halogen atom other than fluorine is reacted with a reducing agent in the presence of an aprotic polar solvent and a catalytic amount of a specific Lewis acid, a 1,2-cis-2-fluorocyclopropane-1-carboxylic ester can be highly and selectively produced at lower temperature within a short period of time. The present invention has been accomplished on the basis of this finding.

Accordingly, the present invention provides a process for producing a compound represented by formula (3):

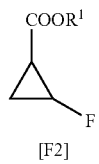

[F2]

[wherein $R^1$ represents a C1-C8 alkyl group, a C6-C12 aryl group, a C2-C8 alkenyl group, or a C7-C26 aralkyl group], which process is characterized by comprising reacting a compound represented by formula (1):

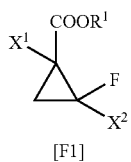

[F1]

[wherein $X^1$ represents a hydrogen atom, a chlorine atom, a bromine atom, or an iodine atom; $X^2$ represents a hydrogen atom, a chlorine atom, a bromine atom, or an iodine atom; when one of $X^1$ and $X^2$ is a chlorine atom, a bromine atom, or an iodine atom, the other is a hydrogen atom; i.e., $X^1$ and $x^2$ are not simultaneously hydrogen atoms; and $R^1$ has the same meaning as defined in formula (3)] with a reducing agent represented by formula (2):

$$M^1BH_mR^2_n \qquad (2\text{-}1)$$

or

$$M^2(BH_mR^2_n)_2 \qquad (2\text{-}2)$$

[wherein $M^1$ represents an alkali metal atom; $M^2$ represents an alkaline earth metal atom or a zinc atom; $R^2$ represents a hydrogen atom, a cyano group, a C1-C8 acyloxy group, or a C1-C6 alkoxy group; m represents an integer from 1 to 4; n represents an integer from 0 to 3; and the sum of m and n is 4] in the presence of an aprotic polar solvent, and one or more Lewis acids selected from among halides and trifluoromethanesulfonic acid salts (triflates) of an atom selected from among boron, magnesium, aluminum, silicon, scandium, titanium, chromium, manganese, iron, cobalt, nickel, copper, zinc, gallium, germanium, yttrium, zirconium, silver, cadmium, indium, tin, antimony, hafnium, lead, bismuth, lanthanum, cerium, and ytterbium.

Effects of the Invention

According to the production process of the present invention, the time required for dehalogenation of a 2-fluorocyclopropane-1-carboxylic ester having, at position 1 or 2, a halogen atom other than fluorine can be considerably reduced, and a 1,2-cis-2-fluorocyclopropane-1-carboxylic ester can be highly selectively produced at high yield. The production process of the present invention is industrially useful as a process for producing 1,2-cis-2-fluorocyclopropane-1-carboxylic acid, which is a raw material for the synthesis of new quinolone antibacterial agents.

Best Mode for Carrying Out the Invention

Compounds of formula (1) (i.e., raw material) are classified into two types: one is a compound wherein $X^1$, which may be a leaving halogen atom (chlorine, bromine, or iodine), is located on the carbon atom (position 1) to which the carboxylic ester moiety is bonded; and the other is a compound wherein $X^2$, which may be a leaving halogen atom, is located on the carbon atom (position 2) to which the fluorine atom is bonded. When one of $X^1$ and $X^2$ is a leaving halogen atom, the other is a hydrogen atom. This excludes both the case where each of $X^1$ and X2 is a hydrogen atom and the case where each of $X^1$ and $X^2$ is a leaving halogen atom. The halogen atom represented by $X^1$ or $X^2$ is chlorine, bromine, or iodine, and preferably a chlorine atom. Specifically, two types of compounds of formula (1) are as follows.

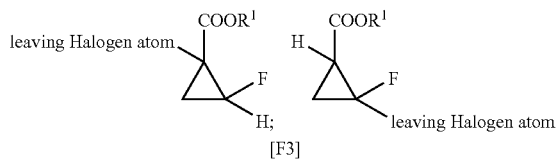

[F3]

The C1-C8 alkyl group represented by $R^1$ may be a linear, branched, or cyclic C1-C8 alkyl group. Examples of the C1-C8 alkyl group include methyl, ethyl, propyl, isopropyl, butyl, isobutyl, sec-butyl, tert-butyl, pentyl, neopentyl, hexyl, cyclopropyl, cyclobutyl, cyclopentyl, and cyclohexyl.

Examples of the C2-C8 alkenyl group include vinyl, allyl, isopropenyl, 2-butenyl, 2-methylallyl, 1,1-dimethylallyl, 3-methyl-2-butenyl, 3-methyl-3-butenyl, 4-pentenyl, hexenyl, octenyl, cyclopropenyl, cyclobutenyl, cyclopentenyl, and cyclohexenyl.

Examples of the C6-C12 aryl group include phenyl and naphthyl. The aryl group may be substituted with, for example, a C1-C6 alkyl group such as methyl, ethyl, propyl, isopropyl, butyl, isobutyl, sec-butyl, or tert-butyl; a C1-C6 alkoxy group such as methoxy, ethoxy, propoxy, or butoxy; a cyano group; a nitro group; any of the aforementioned halogen atoms; an amino group; a hydroxyl group; or a carboxyl group. No particular limitation is imposed on the position and number of a substituent, but the number of the substituent is preferably 1 to 3.

The "C7-C26 aralkyl group" refers to an aralkyl group formed of any of the aforementioned C6-C12 aryl groups and any of the aforementioned C1-C6 alkyl groups. Examples of such an aralkyl group include benzyl and phenethyl, and a benzyl group is preferred. The aryl group constituting the aralkyl group may be substituted with any of the aforementioned substituents.

Of the aforementioned groups represented by $R^1$, a C1-C8 alkyl group is preferred, and a methyl group, an ethyl group, a propyl group, a butyl group, an isobutyl group, a sec-butyl group, or a tert-butyl group is more preferred, with a tert-butyl group being particularly preferred.

Any of compounds of formula (1) can be produced through a known method. For example, such a compound can be easily synthesized from 1-tert-butyl 1-chloro-cyclopropane-1,2-dicarboxylate through the method described in JP-A-1993-301827. Compounds (1) are classified into two isomers in accordance with the configuration of the fluorine atom at position 2 and the carboxylic ester moiety at position 1; i.e., an isomer in which the fluorine atom at position 2 and the carboxylic ester moiety at position 1 are on the same side with respect to the plane of the cyclopropane ring (hereinafter the isomer may be referred to as a "cis-isomer"); and an isomer in which the fluorine atom at position 2 and the carboxylic ester moiety at position 1 are on the opposite side with respect to the plane of the cyclopropane ring (hereinafter the isomer may be referred to as a "trans-isomer").

In the present invention, a critical point is to employ the following three species in combination: a reducing agent of formula (2), a Lewis acid, and an aprotic polar solvent. When any one of these species is not employed, a compound of formula (3) fails to be produced in a highly selective manner at high yield within a short period of time. For example, when no Lewis acid is employed, as described below in Comparative Examples 1 and 2, yield becomes low. Meanwhile, when any solvent other than an aprotic polar solvent is employed, as described in Comparative Examples 3 through 11, virtually no reaction proceeds, or yield and selectivity become low. Thus, when an aprotic polar solvent is employed, reaction in the process of the present invention is completed within a short period of time, and high yield is attained. Therefore, conceivably, an aprotic polar solvent does not serve merely as a reaction solvent, but acts directly on reductive dehalogenation.

Examples of the Lewis acid which may be employed in the present invention include halides of an atom selected from among boron, magnesium, aluminum, silicon, scandium, titanium(IV), chromium(II, III, or IV), manganese, iron(II or III), cobalt, nickel, copper(I or II), zinc, gallium, germanium, yttrium, zirconium, silver, cadmium, indium, tin(II or IV), antimony(III or IV), hafnium, lead, bismuth, lanthanum, cerium, and ytterbium; and trifluoromethanesulfonic acid salts (triflates) of such an atom. Of these halides, a chloride is preferred, and aluminum chloride, silane chloride, scandium chloride, chromium chloride, manganese chloride, iron(II or III) chloride, cobalt chloride, nickel chloride, copper(I or II) chloride, germanium chloride, zirconium chloride, silver chloride, indium chloride, tin(II) chloride, antimony(III) chloride, lead chloride, bismuth chloride, or a boron trifluoride-ether complex is more preferred, with aluminum chloride, iron(II) chloride, cobalt chloride, lead chloride, silver chloride, or indium chloride being particularly preferred. Of the aforementioned triflates, scandium triflate, copper triflate, silver triflate, tin triflate, or hafnium triflate is preferred, and scandium triflate, silver triflate, or hafnium triflate is particularly preferred. Such a Lewis acid may be in the form of hydrate. Such a Lewis acid may form a complex with a solvent. These Lewis acids may be employed singly or in combination of two or more species.

No particular limitation is imposed on the amount of a Lewis acid to be employed, but its amount is preferably 0.01 to 100 mol %, particularly preferably 0.1 to 10 mol %, with respect to a compound of formula (1).

The reducing agent to be employed in the present invention is a metal borohydride compound represented by formula (2-1) or (2-2). Examples of the alkali metal atom shown in formula (2-1) include lithium, sodium, and potassium; and examples of the alkaline earth metal atom shown in formula (2-2) include magnesium, calcium, and strontium. Also, zinc is preferably employed. Of these metal atoms, lithium, sodium, calcium, or zinc is preferred, and lithium, sodium, or zinc is more preferred, with sodium being particularly preferred. When n of formula (2-1) or (2-2) is an integer of 1 or more, the metal borohydride compound has a substituent $R^2$ selected from among a cyano group, a C1-C8 acyloxy group, and a C1-C6 alkoxy group. The substituent $R^2$ is preferably a cyano group or a C1-C8 acyloxy group. Examples of the C1-C8 acyloxy group include formyloxy, acetyloxy, propionyloxy, butyryloxy, valeryloxy, pivaloyloxy, benzoyloxy, benzylcarbonyloxy, and trifluoroacetyloxy. The C1-C6 alkoxy group may be, for example, any of the aforementioned ones.

Specific examples of such a metal borohydride compound include sodium borohydride, lithium borohydride, zinc borohydride, sodium cyanoborohydride, and sodium alkoxyborohydride. Sodium borohydride is particularly preferred. The alkoxy group of sodium alkoxyborohydride is preferably a C1-C6 alkoxy group such as methoxy, ethoxy, or n-butoxy.

Such a metal borohydride compound may be a commercially available one. The metal borohydride compound to be employed in the present invention may be prepared upon use, since most metal borohydride compounds (e.g., zinc borohydride and sodium cyanoborohydride) can be easily prepared from sodium borohydride and a metallic compound or a cyano compound. In the present invention, when a metal borohydride compound to be employed is prepared upon use, preferably, the metal borohydride compound is prepared firstly, and subsequently a compound of formula (1) is added to the resultant reaction mixture.

The amount of the reducing agent to be employed is preferably 1.1 to 3 mol, particularly preferably 1.5 to 2 mol, on the basis of 1 mol of a compound of formula (1).

As described above, the production process of the present invention must be performed in the presence of an aprotic polar solvent. Examples of such an aprotic polar solvent include amide solvents such as N,N-dimethylformamide (DMF), N,N-dimethylacetamide (DMAc), and N-methyl-2-pyrrolidone (NMP); cyclic urea solvents such as 1,3-dimethyl-2-imidazolidinone (DMI) and 1,3-dimethyl-3,4,5,6-tetrahydro-2(1H)-pyrimidinone (DMPU); acetonitrile;. and acetic acid esters. Of these, amide solvents, cyclic urea solvents, or acetic acid esters are preferred. Amide solvents or cyclic urea solvents are more preferred, and specific examples include N,N-dimethylacetamide (DMAc), N-methyl-2-pyrrolidone (NMP), 1,3-dimethyl-2-imidazolidinone (DMI), and 1,3-dimethyl-3,4,5,6-tetrahydro-2(1H)-pyrimidinone (DMPU). Of these, amide solvents are preferred, and N,N-dimethylacetamide (DMAc) is particularly preferred.

When, in a compound of formula (1), a leaving halogen atom is bonded to the carbon atom to which the carboxylic ester moiety is bonded, an acetic acid ester may be employed as an aprotic polar solvent.

These aprotic polar solvents may be employed singly or in combination of two or more species.

So long as the amount of the aforementioned aprotic polar solvent required for performing the reaction of the present invention is ensured, any solvent other than the aprotic polar solvent may be selected and employed as a reaction solvent. Such a reaction solvent is preferably an aprotic solvent. Examples of the aprotic solvent which may be employed include ethers such as diethyl ether, diisopropyl ether, t-butyl methyl ether, 1,2-dimethoxyethane, tetrahydrofuran, and dioxane; and hydrocarbons such as cyclohexane, benzene, toluene, and xylene.

The amount of the aprotic polar solvent to be employed is preferably 1 to 20 times (v/w), particularly preferably 3 to 10 times (v/w), that of a compound of formula (1). The aforementioned aprotic solvent may account for a portion of the above-described amount of the aprotic polar solvent.

The reaction temperature is preferably 0 to 60° C., particularly preferably 0 to 40° C. When a large amount of heat is generated during the course of reaction, the production process may be performed under cooling.

After completion of reaction, a compound of formula (3) is collected from the resultant reaction mixture through a ordinarily employed procedure. For example, the compound is obtained by subjecting the reaction mixture to extraction, and removing inorganic substances through separation of the aqueous layer, followed by removal of the solvent from the organic layer through evaporation. If necessary, the thus-obtained target product may be further purified by means of, for example, distillation or chromatography.

According to the production process of the present invention, from a mixture of cis and trans isomers of a compound of formula (1), a compound of formula (3) can be produced such that the cis isomer/trans isomer ratio falls within a range of 80.3/19.7 to 97/3; i.e., the cis isomer of a compound of formula (3) can be produced in a highly selective manner. According to the production process of the present invention, the unnecessary isomer (trans isomer) of a compound (1) can be converted into the necessary isomer (cis isomer) of a compound of formula (3), and the cis isomer content of the compound of formula (3) can be increased. In addition, reaction can be completed within a short period of time, and a target product is industrially advantageously produced.

In practice of the process of the present invention, no particular limitation is imposed on the order of addition of a reducing agent of formula (2) and a specific Lewis acid to a compound of formula (1). When these reagents are added in any order, dehalogenation can be allowed to proceed.

1,2-Cis-2-fluorocyclopropane-1-carboxylic acid, which serves as an intermediate for the synthesis of new quinolone antibacterial agents, can be easily produced through the following procedure: a compound of formula (3) produced through the production process of the present invention is hydrolyzed through a ordinarily employed technique, to thereby form 2-fluorocyclopropane-1-carboxylic acid, followed by recrystallization, slurrying, optical resolution, and the like.

The above-described process of the present invention can be applied, instead of a compound represented by formula (1), to a compound represented by formula (4):

[F4]

(4)

[wherein $R^1$ has the same meaning as defined above; R represents a hydrogen atom or $COOR^2$; $R^2$ represents a C1-C8 alkyl group, a C6-C12 aryl group, a C2-C8 alkenyl group, or a C7-C26 aralkyl group; and $X^3$ represents a chlorine atom, a bromine atom, or an iodine atom], whereby a compound represented by formula (5):

[F5]

(5)

[wherein $R^1$ and R have the same meanings as defined above] can be produced.

$R^1$ of a compound represented by formula (4) may be considered to have the same meaning as defined in the case of a compound of formula (1). When R is —COOR$^2$, R$^2$ may be considered to have the same meaning as $R^1$.

In the process of the present invention, addition of a phosphorus compound can activate the aforementioned Lewis acids. No particular limitation is imposed on the phosphorus compound to be added, so long as it can form a complex with any of the aforementioned Lewis acids. Examples of such a phosphorus compound include triphenylphosphine, 1,2-bis(diphenylphosphine)ethane, 1,1'-bis(diphenylphosphine)ferrocene, and N,N'-bis(salicylidene)ethylenediamine. In the case where such an activating agent is added, even when the aforementioned aprotic polar solvent (e.g., an amide) is not added, dehalogenation proceeds.

EXAMPLES

The present invention will next be described in more detail with reference to Examples and Referential Examples, which should not be construed as limiting the invention thereto.

The following abbreviations represent corresponding solvents and groups.

NMP: N-methyl-2-pyrrolidone
DMAc: N,N-dimethylacetamide
DMI: 1,3-dimethyl-2-imidazolidinone
DMPU: 1,3-dimethyl-3,4,5,6-tetrahydro-2(1H)-pyrimidinone
THF: tetrahydrofuran
MTBE: methyl t-butyl ether
OTf: trifluoromethanesulfonic acid salt Example 1

Production of tert-butyl
2-fluoro-cyclopropane-1-carboxylate (3a)

Sodium borohydride (8.75 g, 231.21 mmol) was dissolved in NMP (95 mL) under stirring with a stirring blade at room temperature. Subsequently, to the resultant solution was added an NMP solution (20 mL) of tert-butyl 1-chloro-2-fluoro-cyclopropane-1-carboxylate (cis/trans=62/38) (hereinafter the compound will be referred to as "compound (1a)") (30 g, 154.14 mmol). An NMP solution (35 mL) of cobalt chloride hexahydrate (1.1 g, 4.62 mmol) was gradually added to the resultant reaction mixture under ice cooling. After completion of dropwise addition, the resultant mixture was stirred with a stirring blade at room temperature for 30 minutes, and at 40° C. for three hours. After completion of reaction, water (120 mL) was added to the resultant reaction mixture at the same temperature, followed by addition of 5 N hydrochloric acid (30 mL). Subsequently, toluene was added to the reaction mixture for extraction. The resultant toluene layer was washed with water, and then dried over sodium sulfate, to thereby yield a toluene solution containing 24.3 g (yield: 98%) of the title compound. Yield was determined by means of high performance liquid chromatography (HPLC) (the same shall apply hereinafter).

HPLC analysis conditions: column: MERCK Chromorith Performance RP-18 100-4.6 mm, mobile phase: pH 4.2 phosphate buffer/acetonitrile=70/30, flow rate: 1.0 mL/min, detection wavelength: 220 nm.

The cis/trans ratio was found to be 94/6 through gas chromatography (GS) analysis.

GS analysis conditions: detector: FDI, column: Glscience NEUTRA BOND-5 (30 m×0.25 mm), sample vaporization chamber temperature: 250° C., detection unit temperature: 250° C., carrier gas: nitrogen (80 kPa), hydrogen (60 kPa), air (50 kPa).

Example 2

Production of tert-butyl
2-fluoro-cyclopropane-1-carboxylate (3a)

Sodium borohydride (8.75 g, 231.21 mmol) was dissolved in NMP (95 mL) under stirring with a stirring blade at room temperature. Subsequently, to the resultant solution was added an NMP solution (15 mL) of compound (1a) (30 g, 154.14 mmol). An NMP solution (40 mL) of indium chloride (340.9 mg, 1.54 mmol) was gradually added to the resultant reaction mixture under ice cooling. After completion of dropwise addition, the resultant mixture was stirred with a stirring blade at room temperature for 18 hours. After completion of reaction, 1 N hydrochloric acid (150 mL) was added to the resultant reaction mixture at the same temperature. Subsequently, toluene was added to the reaction mixture for extraction. The resultant toluene layer was washed with water, and then dried over sodium sulfate, to thereby yield a toluene solution containing 21.0 g (yield: 85%) of the title compound. The cis/trans ratio was found to be 93/7 through gas chromatography analysis.

Examples 3 through 27

Production of tert-butyl
2-fluoro-cyclopropane-1-carboxylate (3a)

The procedure of Example 1 was repeated, except that the Lewis acid was changed, compound (1a) was employed in an amount of 500 mg, and reaction was performed at 50° C., to thereby yield the title compound. The results are shown in Table 1.

TABLE 1

| Ex. | Lewis acid (0.1 mol eq.) | Reaction time (h) | Yield of compound (3a) (%) | Cis/trans |
|---|---|---|---|---|
| 3 | AlCl$_3$ | 5 | 87 | 92/8 |
| 4 | PdCl$_2$ | 22 | 73 | 90/10 |
| 5 | FeCl$_2$ | 4 | 89 | 91/9 |
| 6 | Sc(OTf)$_3$ | 5 | 76 | 91/9 |
| 7 | AgCl | 6 | 74 | 91/9 |
| 8 | PdCl$_2$ | 6 | 85 | 91/9 |
| 9 | SiCl$_4$ | 7 | 81 | 90/10 |
| 10 | SnCl$_2$ | 18 | 73 | 91/9 |
| 11 | Sn(OTf)$_2$ | 18 | 72 | 90/10 |
| 12 | CuCl | 22 | 79 | 92/8 |
| 13 | CuCl$_2$ | 22 | 86 | 91/9 |
| 14 | Cu(OTf)$_2$ | 22 | 84 | 90/10 |
| 15 | ZrCl$_4$ | 24 | 61 | 93/7 |
| 16 | FeCl$_3$ | 21 | 86 | 91/9 |
| 17 | SbCl$_3$ | 22 | 77 | 91/9 |
| 18 | BiCl$_3$ | 22 | 77 | 91/9 |
| 19 | MnCl$_2$ | 22 | 67 | 91/9 |
| 20 | ScCl$_3$ | 24 | 59 | 92/8 |
| 21 | NiCl$_2$ | 18 | 77 | 92/8 |
| 22 | CrCl$_3$ | 21 | 66 | 92/8 |
| 23 | CoCl$_2$ | 1 | 96 | 91/9 |
| 24 | GeCl$_4$ | 21 | 79 | 90/10 |
| 25 | AgOTf | 22 | 80 | 91/9 |
| 26 | Hf(OTf)$_4$ | 22 | 60 | 91/9 |
| 27 | BF$_3$•Et$_2$O | 9 | 79 | 93/7 |

Example 28

Production of tert-butyl
2-fluoro-cyclopropane-1-carboxylate (3a)

Sodium borohydride (8.75 g, 231.21 mmol) was dissolved in DMAc (95 mL) under stirring with a stirring blade at room temperature. Subsequently, to the resultant solution was added a DMAc solution (15 mL) of compound (1a) (30 g, 154.14 mmol). A DMAc solution (40 mL) of cobalt chloride hexahydrate (183 mg, 0.77 mmol) was gradually added to the resultant reaction mixture under ice cooling. After completion of dropwise addition, the resultant mixture was stirred with a stirring blade for 1 hour and 30 minutes at the same temperature, followed by stirring at room temperature for 30 minutes and at 40° C. for 1 hour and 30 minutes. After completion of reaction, 1 N hydrochloric acid 150 mL) was added to the resultant reaction mixture at the same temperature. Subsequently, toluene was added to the reaction mixture for extraction. The resultant toluene layer was washed with water, and then dried over sodium sulfate, to thereby yield a toluene solution containing 24.7 g (yield: 100% ) of the title compound. The cis/trans ratio was found to be 92.5/7.5 through gas chromatography analysis.

Examples 29 through 32

Production of tert-butyl
2-fluoro-propane-1-carboxylate (3a)

The procedure of Example 28 was repeated, except that the Lewis acid was changed, compound (1a) was employed in an amount of 500 mg, and reaction was performed at 50° C., to thereby yield the title compound. The results are shown in

TABLE 2

| Ex. | Lewis acid (0.03 mol eq.) | Reaction time (h) | Yield of compound (3a) (%) | Cis/trans |
|---|---|---|---|---|
| 29 | InCl$_3$ | 5 | 87 | 92/8 |
| 30 | InCl$_3$•4H$_2$O | 5 | 88 | 93/7 |
| 31 | CoCl$_2$ | 1 | 98 | 92/8 |
| 32 | BF$_3$•Et$_2$O | 6 | 89 | 94/6 |

Example 33

Production of tert-butyl
2-fluoro-cyclopropane-1-carboxylate (3a)

Sodium borohydride (146.0 mg, 3.86 mmol) was dissolved in DMI (1 mL) under stirring at room temperature. Subsequently, to the resultant solution was added a DMI solution (0.5 mL) of compound (1a) (500 mg, 2.57 mmol). A DMI solution (1 mL) of cobalt chloride hexahydrate (18.3 mg, 0.08 mmol) was gradually added to the resultant reaction mixture under ice cooling. After completion of dropwise addition, the resultant mixture was stirred at 40° C. for 20 hours. After completion of reaction, 1 N hydrochloric acid (2.5 mL) was added to the resultant reaction mixture at the same temperature. Subsequently, toluene was added to the reaction mixture for extraction. The resultant toluene layer was washed with water, and then dried over sodium sulfate, to thereby yield a toluene solution containing 329.3 mg (yield: 80%) of the title compound. The cis/trans ratio was found to be 95.5/4.5 through gas chromatography analysis.

Example 34

Production of tert-butyl
2-fluoro-cyclopropane-1-carboxylate (3a)

Sodium borohydride (146.0 mg, 3.86 mmol) was dissolved in DMPU (1 mL) under stirring at room temperature. Subsequently, to the resultant solution was added a DMPU solution (0.5 mL) of compound (1a) (500 mg, 2.57 mmol). A DMPU solution (1 mL) of cobalt chloride hexahydrate (18.3 mg, 0.08 mmol) was gradually added to the resultant reaction mixture under ice cooling. After completion of dropwise addition, the resultant mixture was stirred at 40° C. for 20 hours. After completion of reaction, 1 N hydrochloric acid (2.5 mL) was added to the resultant reaction mixture at the same temperature. Subsequently, toluene was added to the reaction mixture for extraction. The resultant toluene layer was washed with water, and then dried over sodium sulfate, to thereby yield a toluene solution containing 300.4 mg (yield: 73%) of the title compound. The cis/trans ratio was found to be 97/3 through gas chromatography analysis.

Example 35

Production of tert-butyl
2-fluoro-cyclopropane-1-carboxylate (3a)

Sodium borohydride (340.3 mg, 9.0 mmol) was dissolved in ethyl acetate (1 mL) under stirring at room temperature. Subsequently, to the resultant solution was added an ethyl acetate solution (0.5 mL) of compound (1a) (500 mg, 2.57 mmol). An ethyl acetate solution (1 mL) of cobalt chloride hexahydrate (18.3 mg, 0.08 mmol) was gradually added to the resultant reaction mixture under ice cooling. After completion of dropwise addition, the resultant mixture was stirred at 40° C. for 40 hours. After completion of reaction, 1 N hydrochloric acid (2.5 mL) was added to the resultant reaction mixture at the same temperature. Subsequently, toluene was added to the reaction mixture for extraction. The resultant toluene layer was washed with water, and then dried over sodium sulfate, to thereby yield a toluene solution containing 362.1 mg (yield: 88%) of the title compound. The cis/trans ratio was found to be 80.3/19.7 through gas chromatography analysis.

Comparative Example 1

Production of tert-butyl
2-fluoro-cyclopropane-1-carboxylate (3a)

The procedure of Example 1 was repeated, except that cobalt chloride hexahydrate was not added, and stirring with a stirring blade was performed at 70° C. for 18 hours after addition of compound (1a), to thereby yield a toluene solution containing 15.1 g (yield: 61%) of the title compound. The cis/trans ratio was found to be 92/8 through gas chromatography analysis.

Comparative Example 2

Production of tert-butyl
2-fluoro-cyclopropane-1-carboxylate (3a)

The procedure of Example 1 was repeated, except that cobalt chloride hexahydrate was not added, and stirring with a stirring blade was performed at 50° C. for 15 hours after addition of compound (1a), to thereby yield a toluene solution containing 2.47 g (yield: 10%) of the title compound. The cis/trans ratio was found to be 90/10 through gas chromatography analysis.

Referential Example 1

Production of 1,2-cis-2-fluorocyclopropane-1-carboxylic acid

To the toluene solution (150 mL) of tert-butyl 2-fluoro-cyclopropane-1-carboxylate (3a) (12.4 g, cis/trans=93/7) obtained in Example 2, p-toluenesulfonic acid monohydrate (732.0 mg, 3.85 mmol) was added, and the resultant mixture was heated under reflux for 1 hour and 30 minutes. After the resultant reaction mixture was cooled, 3.5 N aqueous sodium hydroxide solution (30 mL) was added to the reaction mixture, and the resultant organic layer was separated. Concentrated hydrochloric acid (6.2 mL) was added to the aqueous layer for adjusting the pH to about 1. Subsequently, the aqueous layer was subjected to extraction with methyl tert-butyl ether, and the resultant organic layer was dried over magnesium sulfate. The solvent was removed through evaporation under reduced pressure, to thereby yield 2-fluoro-cyclopropane-1-carboxylic acid (6.75 g, cis/trans=93/7) as an oily substance. To the oily substance, n-heptane (100 mL) was added, followed by slurrying at room temperature for 30 minutes and at −15° C. for 1 hour and 30 minutes. The thus-precipitated crystals were collected through filtration, and then dried, to thereby yield 6.43 g of the title compound as white crystals. The crystals were subjected to gas chromatography analysis, and the cis/trans ratio was found to be 99.2/0.8.

Example 36

Production of ethyl 2-fluoro-cyclopropane-1-carboxylate (3b)

Sodium borohydride (170 mg, 4.50 mmol) was added to and dissolved in N,N-dimethylacetamide (1.5 mL) at room temperature, followed by addition of an N,N-dimethylacetamide solution (1.0 mL) of ethyl 1-chloro-2-fluoro-cyclopropane-1-carboxylate (hereinafter the compound will be referred to as "compound (1b)") (cis/trans=95/5) (500 mg, 3.00 mmol). Cobalt chloride hexahydrate (3.6 mg, 0.015 mmol) was added to the resultant solution at the same temperature. After completion of addition, the resultant mixture was stirred at 40° C. for one hour. After completion of reaction, the whole reaction mixture was diluted with an HPLC mobile phase to 50 mL, to thereby yield a solution containing 381.3 mg (yield: 96%) of the title compound. Yield was determined by means of high performance liquid chromatography (HPLC) (the same shall apply hereinafter).

HPLC analysis conditions: column: GL-Science Inertsil ODS-3V 4.6-150 mm, mobile phase: pH 7.0 phosphate buffer/acetonitrile=70/30, flow rate: 1.0 mL/min, detection wavelength: 220 nm.

The cis/trans ratio was found to be 94/6 through gas chromatography (GS) analysis. GS analysis conditions: detector: FDI, column: GL-Science NEUTRA BOND-5 (30 m ×0.25 mm), oven temperature: 60 to 200° C., sample vaporization chamber temperature: 250° C., detection unit temperature: 250° C., carrier gas: nitrogen (80 kPa), hydrogen (60 kPa), air (50 kPa).

(1b, cis-isomer); $^1$H-NMR (CD$_3$OD) δ: 4.87 (1H, ddd, J=63.2, 6.8, 4.9 Hz), 4.29 (2H, q, J=6.8 Hz), 2.45 (1H, ddd, J=23.4, 8.8, 4.9 Hz), 1.61 (1H, ddd, J=12.2, 8.8, 6.8 Hz), 1.33 (3H, t, J=6.8 Hz).

(1b, trans-isomer); $^1$H-NMR (CD$_3$OD) δ: 4.88 (1H, ddd, J=64.5, 6.8, 4.9 Hz), 4.24 (2H, q, J=7.3 Hz), 1.96 (1H, ddd, J=15.1, 8.3, 6.8 Hz), 1.68 (1H, ddd, J=21.5, 8.3, 4.4 Hz), 1.31 (3H, t, J=7.3 Hz)

(3b, cis-isomer); $^1$H-NMR (CD$_3$OD) δ: 4.73 (1H, dm, J=63.1 Hz), 4.20 (2H, q, J=7.1 Hz), 1.84-1.75 (2H, m), 1.29 (3H, t, J=7.1 Hz), 1.18-1.11 (1H, m).

(3b, trans-isomer); $^1$H-NMR (CD$_3$OD) δ: 4.80 (1H, dm, J=63.5 Hz), 4.14 (2H, q, J=7.1 Hz), 2.11-2.04 (1H, m), 1.49-1.41 (1H, m), 1.27 (3H, t, J=7.1 Hz), 1.34-1.24 (1H, m).

Example 37

Production of ethyl 2-fluoro-cyclopropane-1-carboxylate (3b)

Sodium borohydride (51 mg, 1.35 mmol) was added to and dissolved in N,N-dimethylacetamide (1.5 mL) at room temperature, followed by addition of an N,N-dimethylacetamide solution (1.0 mL) of compound (1b) (cis/trans=6/94) (150 mg, 0.90 mmol). Cobalt chloride hexahydrate (1.2 mg, 0.005 mmol) was added to the resultant solution at the same temperature. After completion of addition, the resultant mixture was stirred at 40° C. for one hour. After completion of reaction, the whole reaction mixture was diluted with an HPLC mobile phase to 25 mL, to thereby yield a solution containing 93.8 mg (yield: 79%) of the title compound. Yield was determined by means of high performance liquid chromatography (HPLC) (the same shall apply hereinafter).

HPLC analysis conditions: column: GL-Science Inertsil ODS-3V 4.6-150 mm, mobile phase: pH 7.0 phosphate buffer/acetonitrile=70/30, flow rate: 1.0 mL/min, detection wavelength: 220 nm.

The cis/trans ratio was found to be 95/5 through gas chromatography (GS) analysis. GS analysis conditions: detector: FDI, column: GL-Science NEUTRA BOND-5 (30 m×0.25 mm), oven temperature: 60 to 200° C., sample vaporization chamber temperature: 250° C., detection unit temperature: 250° C., carrier gas: nitrogen (80 kPa), hydrogen (60 kPa), air (50 kPa).

Example 38

Production of methyl 2-fluoro-cyclopropane-1-carboxylate (3c)

Sodium borohydride (186 mg, 4.92 mmol) was added to and dissolved in N,N-dimethylacetamide (1.5 mL) at room temperature, followed by addition of an N,N-dimethylacetamide solution (1.0 mL) of methyl 1-chloro-2-fluoro-cyclopropane-1-carboxylate (hereinafter the compound will be referred to as "compound (1c)") (cis/trans=95/5) (500 mg, 3.27 mmol). Cobalt chloride hexahydrate (3.9 mg, 0.016 mmol) was added to the resultant solution at the same temperature. After completion of addition, the resultant mixture was stirred at 40° C. for one hour. After completion of reaction, the whole reaction mixture was diluted with an HPLC mobile phase to 50 mL, to thereby yield a solution containing 386.2 mg (yield: 93%) of the title compound. Yield was determined by means of high performance liquid chromatography (HPLC) (the same shall apply hereinafter).

HPLC analysis conditions: column: GL-Science Inertsil ODS-3V 4.6-250 mm, mobile phase: pH 7.0 phosphate buffer/acetonitrile=70/30, flow rate: 1.0 mL/min, detection wavelength: 220 nm.

The cis/trans ratio was found to be 95/5 through gas chromatography (GS) analysis. GS analysis conditions: detector: FDI, column: GL-Science NEUTRA BOND-5 (30 m×0.25 mm), oven temperature: 60 to 200° C., sample vaporization chamber temperature: 250° C., detection unit temperature: 250° C., carrier gas: nitrogen (80 kPa), hydrogen (60 kPa), air (50 kPa).

(1c, cis-isomer); $^1$H-NMR (CD$_3$OD) δ: 4.88 (1H, ddd, J=63.0, 6.8, 4.9 Hz), 3.85 (3H, s), 2.46 (1H, ddd, J=23.4, 8.8, 4.9 Hz), 1.63 (1H, ddd, J=12.2, 8.8, 6.8 Hz).

(1c, trans-isomer); $^1$H-NMR (CD$_3$OD) δ: 4.88 (1H, ddd, J=64.5, 6.8, 4.4 Hz), 3.80 (3H, s), 1.98 (1H, ddd, J=16.6, 8.3, 6.8 Hz), 1.69 (1H, ddd, J=21.5, 8.3, 4.4 Hz).

(3c, cis-isomer); $^1$H-NMR (CD$_3$OD) δ: 4.73 (1H, dtd, J=64.7, 6.4, 3.9 Hz), 3.74 (3H, s), 1.86-1.75 (2H, m), 1.21-1.12 (1H, m).

(3c, trans-isomer); $^1$H-NMR (CD$_3$OD) δ: 4.81 (1H, dddd, J=64.0, 6.8, 3.4, 1.5 Hz), 3.69 (3H, s), 2.09 (1H, dddd, J=17.3, 10.5, 6.8, 3.4 Hz), 1.47 (1H, dddd, J=21.4, 10.5, 6.8, 3.4 Hz), 1.32 (1H, dq, J=6.8, 1.3 Hz).

Example 39

Production of methyl 2-fluoro-cyclopropane-1-carboxylate (3c)

Sodium borohydride (112 mg, 2.96 mmol) was added to and dissolved in N,N-dimethylacetamide (1.5 mL) at room temperature, followed by addition of an N,N-dimethylacetamide solution (1.0 mL) of compound (1c) (cis/trans=2/98) (300 mg, 1.97 mmol). Cobalt chloride hexahydrate (2.8 mg, 0.010 mmol) was added to the resultant solution at the same temperature. After completion of addition, the resultant mixture was stirred at 40° C. for one hour. After completion of reaction, the whole reaction mixture was diluted with an HPLC mobile phase to 50 mL, to thereby yield a solution containing 232.7 mg (yield: 69%) of the title compound. Yield was determined by means of high performance liquid chromatography (HPLC) (the same shall apply hereinafter).

HPLC analysis conditions: column: GL-Science Inertsil ODS-3V 4.6-250 mm, mobile phase: pH 7.0 phosphate buffer/acetonitrile=70/30, flow rate: 1.0 mL/min, detection wavelength: 220 nm.

The cis/trans ratio was found to be 95/5 through gas chromatography (GS) analysis. GS analysis conditions: detector: FDI, column: GL-Science NEUTRA BOND-5 (30 m×0.25 mm), oven temperature: 60 to 200° C., sample vaporization chamber temperature: 250° C., detection unit temperature: 250° C., carrier gas: nitrogen (80 kPa), hydrogen (60 kPa), air (50 kPa).

Example 40

Production of tert-butyl 2-fluoro-cyclopropane-1-carboxylate (3a)

Sodium borohydride (243 mg, 6.43 mmol) was added to and dissolved in N,N-dimethylacetamide (1.5 mL) at room temperature, followed by addition of an N,N-dimethylacetamide solution (1.0 mL) of tert-butyl 2-chloro-2-fluoro-cyclopropane-1-carboxylate (cis/trans=57/43) (hereinafter the compound will be referred to as "compound (1d)") (500 mg, 2.57 mmol). Cobalt chloride (33.4 mg, 1.54 mmol) was added to the resultant solution. After completion of addition, the resultant mixture was stirred at 50° C. for 14 hours. After completion of reaction, the whole reaction mixture was diluted with an HPLC mobile phase to 50 mL, to thereby yield a solution containing 344.6 mg (yield: 84%) of the title compound. Yield was determined by means of high performance liquid chromatography (HPLC) (the same shall apply hereinafter).

HPLC analysis conditions: column: GL-Science Inertsil ODS-3V 4.6-150 mm, mobile phase: pH 7.0 phosphate buffer/acetonitrile=50/50, flow rate: 1.0 mL/min, detection wavelength: 220 nm.

The cis/trans ratio was found to be 67/33 through gas chromatography (GS) analysis. GS analysis conditions: detector: FDI, column: GL-Science NEUTRA BOND-5 (30 m×0.25 mm), oven temperature: 60 to 200° C., sample vaporization chamber temperature: 250° C., detection unit temperature: 250° C., carrier gas: nitrogen (80 kPa), hydrogen (60 kPa), air (50 kPa)

Compound (1d) was produced through a ordinarily employed procedure. Specifically, compound (1d) was produced through the following procedure: ethyl 1-chloro-2-fluoro-cyclopropane-1-carboxylate (compound (1b)) was hydrolyzed under alkaline conditions, to thereby convert compound (1b) into a corresponding carboxylic acid compound; and subsequently the carboxylic acid compound was subjected to esterification in t-butanol/methylene chloride in the presence of a sulfuric acid catalyst.

(1d, cis-isomer); $^1$H-NMR (CD$_3$OD) δ: 2.39 (1H, ddd, J=10.1, 7.9, 1.1 Hz), 2.08 (1H, ddd, J=32.0, 16.0, 8.0 Hz), 1.93-1.86 (1H, m), 1.47 (9H, s)

(1d, trans-isomer); $^1$H-NMR (CD$_3$OD) 6: 2.55 (1H, ddd, J=17.9, 9.6, 7.3 Hz), 1.90 (1H, ddd, J=16.9, 9.3, 6.3 Hz), 1.93-1.86 (1H, m), 1.48 (9H, s)

(3a, cis-isomer); $^1$H-NMR (CD$_3$OD) δ: 4.68 (1H, ddt, J=66.2, 10.9, 3.5 Hz), 1.75-1.65 (2H, m), 1.48 (9H, s), 1.08-1.02 (1H, m).

(3a, trans-isomer); $^1$H-NMR (CD$_3$OD) δ: 4.74 (1H, ddt, J=64.3, 9.6, 1.7 Hz), 2.03-1.94 (1H, m), 1.44 (9H, s), 1.42-1.32 (1H, m).

Examples 41 through 49

Production of tert-butyl 2-fluoro-cyclopropane-1-carboxylate (3a)

The procedure of Example 40 was repeated by use of compound (1d) (500 mg), except that the Lewis acid was changed, to thereby yield the title compound. The results are shown in Table 3.

TABLE 3

| Ex. | Lewis acid (0.1 mol eq.) | Reaction time (h) | Yield of compound (3a) (%) | Cis/trans |
|---|---|---|---|---|
| 41 | CoBr$_2$ | 15 | 82 | 66/34 |
| 42 | CoI$_2$ | 15 | 81 | 66/34 |
| 43 | FeCl$_2$ | 3 | 82 | 60/40 |
| 44 | AlCl$_3$ | 5 | 94 | 61/39 |
| 45 | PbCl$_2$ | 5 | 92 | 64/36 |
| 46 | AgCl | 7 | 93 | 62/38 |
| 47 | InCl$_3$ | 14 | 92 | 63/37 |
| 48 | In(OTf)$_3$ | 22 | 85 | 66/34 |
| 49 | Sc(OTf)$_3$ | 22 | 81 | 66/34 |

Comparative Examples 3 through 11

Production of tert-butyl 2-fluoro-cyclopropane-1-carboxylate (3a)

The procedure of Example 40 was repeated by use of compound (1d) (500 mg), except that the solvent was changed, to thereby yield the title compound. The results are shown in Table 4.

TABLE 4

| Comp. Ex. | Solvent | Reaction time (h) | Yield of compound (3a) (%) | Cis/trans |
|---|---|---|---|---|
| 3 | EtOH | 22 | 7 | 82/18 |
| 4 | 2-Propanol | 22 | 27 | 31/69 |
| 5 | H₂O | 22 | 0 | — |
| 6 | MeOH | 22 | 0 | — |
| 7 | THF | 22 | 0 | — |
| 8 | MTBE | 22 | 0 | — |
| 9 | Toluene | 22 | 0 | — |
| 10 | Cyclohexane | 22 | 0 | — |
| 11 | Heptane | 22 | 0 | — |

Comparative Example 12

Production of tert-butyl 2-fluoro-cyclopropane-1-carboxylate (3a)

The procedure of Example 40 was repeated, except that compound (1d) was replaced by compound (1a), and cobalt chloride was not added after addition of compound (1a), to thereby yield a solution containing 170.9 mg (yield: 42%) of the title compound. The cis/trans ratio was found to be 71/29 through gas chromatography analysis.

Example 50

Production of tert-butyl 2-fluoro-cyclopropane-1-carboxylate (3a)

Sodium borohydride (243 mg, 6.43 mmol) was added to and dissolved in N,N-dimethylacetamide (1.5 mL) at room temperature, followed by addition of an N,N-dimethylacetamide solution (1.0 mL) of compound (1d) (500 mg, 2.57 mmol). Cobalt chloride (33.4 mg, 1.54 mmol) was added to the resultant solution. After completion of addition, the resultant mixture was stirred at 40° C. for 21 hours. After completion of reaction, the whole reaction mixture was diluted with an HPLC mobile phase to 50 mL, to thereby yield a solution containing 375.9 mg (yield: 91%) of the title compound. Yield was determined by means of high performance liquid chromatography (HPLC) (the same shall apply hereinafter).

HPLC analysis conditions: column: GL-Science Inertsil ODS-3V 4.6-150 mm, mobile phase: pH 7.0 phosphate buffer/acetonitrile=50/50, flow rate: 1.0 mL/min, detection wavelength: 220 nm.

The cis/trans ratio was found to be 96/4 through gas chromatography (GS) analysis. GS analysis conditions: detector: FDI, column: GL-Science NEUTRA BOND-5 (30 m×0.25 mm), oven temperature: 60 to 200° C., sample vaporization chamber temperature: 250° C., detection unit temperature: 250° C., carrier gas: nitrogen (80 kPa), hydrogen (60 kPa), air (50 kPa).

Example 51

Production of tert-butyl cyclopropane carboxylate (5a)

Sodium borohydride (161 mg, 4.25 mmol) was added to and dissolved in N,N-dimethylacetamide (1.5 mL) at room temperature, followed by addition of an N,N-dimethylacetamide solution (1.0 mL) of tert-butyl 1-chlorocyclopropane-1-carboxylate (hereinafter the compound will be referred to as "compound (4a)") (500 mg, 2.83 mmol) at 10C. Cobalt chloride hexahydrate (3.3 mg, 0.014 mmol) was added to the resultant solution. After completion of addition, the resultant mixture was stirred at 40° C. for 21 hours. After completion of reaction, the whole reaction mixture was diluted with an HPLC mobile phase to 50 mL, to thereby yield a solution containing 320.3 mg (yield: 80%) of the title compound. Yield was determined by means of high performance liquid chromatography (HPLC) (the same shall apply hereinafter).

HPLC analysis conditions: column: GL-Science Inertsil ODS-3V 4.6-150 mm, mobile phase: pH 7.0 phosphate buffer/acetonitrile=50/50, flow rate: 1.0 mL/min, detection wavelength: 220 nm.

Compound (4a) was produced through a ordinarily employed procedure. Specifically, compound (4a) was produced through the following procedure: 1-chloro-1-(tetrachlorovinyl)-cyclopropane was oxidized with sodium periodate in water/acetonitrile/carbon tetrachloride in the presence of ruthenium chloride, thereby converting the cyclopropane into 1-chlorocyclopropanecarboxylic acid; and subsequently the carboxylic acid compound was subjected to esterification in t-butanol/chloroform in the presence of a sulfuric acid catalyst.

(4a); $^1$H-NMR (CD$_3$OD) δ: 1.56 (2H, dd, J=8.2, 5.0 Hz), 1.46 (9H, s), 1.30 (2H, dd, J=8.3, 5.1 Hz).

(5a); $^1$H-NMR (CD$_3$OD) δ: 1.43 (9H, s), 0.82-0.78 (5H, m)

Comparative Example 13

Production of tert-butyl cyclopropane carboxylate (5a)

The procedure of Example 51 was repeated, except that cobalt chloride hexahydrate was not added after addition of compound (4a), to thereby yield a solution containing 0.0 mg (yield: 0%) of the title compound.

Example 52

Production of di-tert-butyl cyclopropane-1,2-dicarboxylate (5b)

Sodium borohydride (103 mg, 1.81 mmol) was added to and dissolved in N,N-dimethylacetamide (1.5 mL) at room temperature, followed by addition of an N,N-dimethylacetamide solution (1.0 mL) of di-tert-butyl 1-chlorocyclopropane-1,2-dicarboxylate (cis/trans=26/74) (hereinafter the compound will be referred to as "compound (4b)") (500 mg, 1.81 mmol) at 10° C. Cobalt chloride hexahydrate (2.4 mg, 0.010 mmol) was added to the resultant solution at the same temperature. After completion of addition, the resultant mixture was stirred at 40° C. for six hours. After completion of reaction, the whole reaction mixture was diluted with an HPLC mobile phase to 50 mL, to thereby yield a solution containing 418.8 mg (yield: 96%) of the title compound. Yield was determined by means of high performance liquid chromatography (HPLC) (the same shall apply hereinafter).

HPLC analysis conditions: column: GL-Science Inertsil ODS-3V 4.6-150 mm, mobile phase: pH 7.0 phosphate buffer/acetonitrile=40/60, flow rate: 1.0 mL/min, detection wavelength: 220 nm.

The cis/trans ratio was found to be 99/1 through gas chromatography (GS) analysis. GS analysis conditions: detector: FDI, column: GL-Science NEUTRA BOND-5 (30 m×0.25 mm), oven temperature: 60 to 200° C., sample vaporization chamber temperature: 250° C., detection unit temperature: 250° C., carrier gas: nitrogen (80 kPa), hydrogen (60 kPa), air (50 kPa).

Compound (4b) was produced through a ordinarily employed procedure. Specifically, compound (4b) was produced through esterification of 2-chloro-2-tert-butoxycarbonyl-1-cyclopropanecarboxylic acid in t-butanol/chloroform in the presence of a sulfuric acid catalyst.

(4b, cis-isomer); $^1$H-NMR (CD$_3$OD) δ: 2.34 (1H, dd, J=9.6, 7.7 Hz), 1.91 (1H, dd, J=7.8, 6.3 Hz), 1.57 (1H, dd, J=9.8, 6.3 Hz), 1.48 (18H,s).

(4b, trans-isomer); $^1$H-NMR (CD$_3$OD) δ: 2.52 (1H, dd, J=9.2, 7.9 Hz), 1.81 (1H, dd, J=9.3, 5.9 Hz), 1.73 (1H, dd, J=7.8, 5.9 Hz), 1.48 (18H,s).

(5b, cis-isomer); $^1$H-NMR (CD$_3$OD) δ: 1.98 (1H, dd, J=8.2, 6.7 Hz), 1.43 (18H,s), 1.39 (1H, ddd, J=13.4, 6.9, 1.4 Hz), 1.11 (1H, ddd, J=8.3, 4.7, 1.4 Hz).

(5b, trans-isomer); $^1$H-NMR (CD$_3$OD) δ: 2.12 (2H, dt, J=6.0, 3.5 Hz), 1.45 (18H,s), 1.39 (2H, dt, J=6.1, 3.5 Hz).

Comparative Example 14

Production of di-tert-butyl cyclopropane-1,2-dicarboxylate (5b)

The procedure of Example 52 was repeated, except that cobalt chloride hexahydrate was not added after addition of compound (4b), to thereby yield a solution containing 1.3 mg (yield: 0.3%) of the title compound.

Example 53

Production of di-tert-butyl cyclopropane-1,2-dicarboxylate (5b)

Sodium borohydride (35.7 mg, 0.944 mmol) was added to and dissolved in N,N-dimethylacetamide (1.5 mL) at room temperature, followed by addition of an N,N-dimethylacetamide solution (1.0 mL) of di-tert-butyl 1-bromocyclopropane-1,2-dicarboxylate (cis/trans=11/89) (hereinafter the compound will be referred to as "compound (4c)") (202 mg, 0.629 mmol) at 10° C. Without manipulating the temperature of the reaction, cobalt chloride hexahydrate (0.7 mg, 0.003 mmol) was added to the resultant solution. After completion of addition, the resultant mixture was stirred at 10° C. for 15 minutes. After completion of reaction, the entirety of the reaction mixture was diluted with an HPLC mobile phase to 20 mL, to thereby yield a solution containing 152.4 mg (yield: 100%) of the title compound. Yield was determined by means of high performance liquid chromatography (HPLC) (the same shall apply hereinafter).

HPLC analysis conditions: column: GL-Science Inertsil ODS-3V 4.6-150 mm, mobile phase: pH 7.0 phosphate buffer/acetonitrile=40/60, flow rate: 1.0 mL/min, detection wavelength: 220 nm.

The cis/trans ratio was found to be 99/1 through gas chromatography (GS) analysis. GS analysis conditions: detector: FDI, column: GL-Science NEUTRA BOND-5 (30 m×0.25 mm), oven temperature: 60 to 200° C., sample vaporization chamber temperature: 250° C., detection unit temperature: 250° C., carrier gas: nitrogen (80 kPa), hydrogen (60 kPa), air (50 kPa).

Compound (4c) was produced through a ordinarily employed procedure. Specifically, compound (4c) was produced through reaction between tert-butyl bromoacetate and tert-butyl α-bromoacrylate in N,N-dimethylformamide in the presence of sodium hydride serving as a base.

(4c, cis-isomer); $^1$H-NMR (CD$_3$OD) δ: 2.32 (1H, dd, J=9.4, 7.2 Hz), 1.89 (1H, dd, J=7.1, 6.6 Hz), 1.57 (1H, dd, J=9.5, 6.6 Hz), 1.47 (18H,s).

(4c, trans-isomer); $^1$H-NMR (CD$_3$OD) δ: 2.44 (1H, dd, J=9.3, 7.8 Hz), 1.83 (1H, dd, J=9.3, 5.9 Hz), 1.71 (1H, dd, J=7.7, 6.0 Hz), 1.47 (18H,s).

Example 54

Production of tert-butyl 2-fluoro-cyclopropane-1-carboxylate (3a)

Sodium borohydride (292 mg, 7.71 mmol) was added to and suspended in acetonitrile (1.5 mL) at room temperature, followed by addition of an acetonitrile solution (1.0 mL) of compound (1a) (cis/trans=62/38) (500 mg, 2.57 mmol). Cobalt chloride (10 mg, 0.077 mmol) and N,N-dimethylacetamide (14 µL, 0.154 mmol) were added to the resultant solution at the same temperature. After completion of addition, the resultant mixture was stirred at room temperature for 15 hours. After completion of reaction, the whole reaction mixture was diluted with an HPLC mobile phase to 50 mL, to thereby yield a solution containing 355.7 mg (yield: 86%) of the title compound. Yield was determined by means of high performance liquid chromatography (HPLC) (the same shall apply hereinafter).

HPLC analysis conditions: column: GL-Science Inertsil ODS-3V 4.6-150 mm, mobile phase: pH 7.0 phosphate buffer/acetonitrile=50/50, flow rate: 1.0 mL/min, detection wavelength: 220 nm.

The cis/trans ratio was found to be 81/19 through gas chromatography (GS) analysis. GS analysis conditions: detector: FDI, column: GL-Science NEUTRA BOND-5 (30 m×0.25 mm), oven temperature: 60 to 200° C., sample vaporization chamber temperature: 250° C., detection unit temperature: 250° C., carrier gas: nitrogen (80 kPa), hydrogen (60 kPa), air (50 kPa).

Comparative Example 15

Production of tert-butyl 2-fluoro-cyclopropane-1-carboxylate (3a)

The procedure of Example 54 was repeated, except that N,N-dimethylacetamide was not added after addition of compound (1a) and cobalt chloride, to thereby yield a solution containing 0.0 mg (yield: 0%) of the title compound.

Example 55

Production of tert-butyl 2-fluoro-cyclopropane-1-carboxylate (3a)

Sodium borohydride (146 mg, 3.86 mmol) was added to and dissolved in ethanol (1.5 mL) at room temperature, followed by addition of an ethanol solution (1.0 mL) of compound (1a) (cis/trans 62/38) (500 mg, 2.57 mmol).

Dichlorobis(triphenylphosphine)cobalt (168 mg, 0.257 mmol) was added to the resultant solution at the same temperature. After completion of addition, the resultant mixture was stirred at 40° C. for 16 hours. After completion of reaction, the whole reaction mixture was diluted with an HPLC mobile phase to 50 mL, to thereby yield a solution containing 307.9 mg (yield: 75%) of the title compound. Yield was determined by means of high performance liquid chromatography (HPLC).

HPLC analysis conditions: column: GL-Science Inertsil ODS-3V 4.6-150 mm, mobile phase: pH 7.0 phosphate buffer/acetonitrile=50/50, flow rate: 1.0 mL/min, detection wavelength: 220 nm.

The cis/trans ratio was found to be 63/37 through gas chromatography (GS) analysis. GS analysis conditions: detector: FDI, column: GL-Science NEUTRA BOND-5 (30 m×0.25 mm), oven temperature: 60 to 200° C., sample vaporization chamber temperature: 250° C., detection unit temperature: 250° C., carrier gas: nitrogen (80 kPa), hydrogen (60 kPa), air (50 kPa).

Example 56

Production of tert-butyl 2-fluoro-cyclopropane-1-carboxylate (3a)

The procedure of Example 55 was repeated by use of compound (1a), except that acetonitrile was employed as a solvent, to thereby yield a solution containing 152.7 mg (yield: 37%) of the title compound. The cis/trans ratio was found to be 72/28 through gas chromatography analysis.

INDUSTRIAL APPLICABILITY

Employment of the process of the present invention can considerably reduce the time required for dehalogenation of a 2-cyclopropane-1-carboxylic ester having, at position 1 or 2, a halogen atom other than fluorine, and increase reaction yield, as compared with the case of a conventional method. Particularly, even when an apparatus under the assumption of industrial production is employed, reaction can be completed within a short period of time. Therefore, the process of the present invention can be industrially employed as a process for producing a raw material for the synthesis of new quinolone antibacterial agents.

The invention claimed is:

1. A process for producing a compound represented by formula (3):

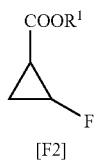

(3)

wherein $R^1$ represents a C1-C8 alkyl group, a C6-C12 aryl group, a C2-C8 alkenyl group, or a C7-C26 aralkyl group, which process comprises reacting a compound represented by formula (1):

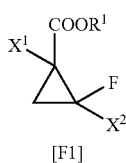

(1)

wherein $X^1$ is a hydrogen atom, and $X^2$ is a chlorine atom, a bromine atom, or an iodine atom, with a reducing agent represented by formula (2):

or

wherein $M^1$ represents an alkali metal atom; $M^2$ represents an alkaline earth metal atom or a zinc atom; $R^2$ represents a hydrogen atom, a cyano group, a C1-C8 acyloxy group, or a C1-C6 alkoxy group; m represents an integer from 1 to 4; n represents an integer from 0 to 3; and the sum of m and n is 4, in the presence of an aprotic polar solvent, and one or more Lewis acids selected from among halides and trifluoromethanesulfonic acid salts (triflates) of an atom selected from among boron, magnesium, aluminum, silicon, scandium, titanium, chromium, manganese, iron, cobalt, nickel, copper, zinc, gallium, germanium, yttrium, zirconium, silver, cadmium, indium, tin, antimony, hafnium, lead, bismuth, lanthanum, cerium, and ytterbium.

2. A production process according to claim 1, wherein $X^1$ is a hydrogen atom, and $X^2$ is a chlorine atom.

3. A production process according to claim 1, wherein $R^1$ is a C1-C8 alkyl group.

4. A production process according to claim 3, wherein the C1-C8 alkyl group is a tert-butyl group.

5. A production process according to claim 1, wherein the aprotic solvent is an amide solvent or a cyclic urea solvent.

6. A production process according to claim 1, wherein the aprotic solvent is an amide solvent.

7. A production process according to claim 1, wherein the amide solvent is one or more solvents selected from among N,N-dimethylformamide (DMF), N,N-dimethylacetamide (DMAc), and N-methyl-2-pyrrolidone.

8. A production process according to claim 1, wherein the aprotic polar solvent is one or more solvents selected from among N,N-dimethylacetamide (DMAc), N-methyl-2-pyrrolidone (NMP), 1,3-dimethyl-2-imidazolidinone (DMI), and 1,3-dimethyl-3,4,5,6-tetrahydro-2(1H)-pyrimidinone (DMPU).

9. A production process according to claim 1, wherein the aprotic polar solvent is N,N-dimethylacetamide (DMAc).

10. A production process according to claim 1, wherein the Lewis acid is aluminum chloride, silane chloride, scandium chloride, chromium chloride, manganese chloride, iron(II or III) chloride, cobalt chloride, nickel chloride, copper(I or II) chloride, germanium chloride, zirconium chloride, silver chloride, indium chloride, tin(II) chloride, antimony(III) chloride, lead chloride, bismuth chloride, a boron trifluoride-ether complex, scandium triflate, copper triflate, silver triflate, tin triflate, or hafnium triflate.

11. A production process according to claim 1, wherein the Lewis acid is aluminum chloride, iron(II) chloride, cobalt chloride, lead chloride, silver chloride, or indium chloride.

12. A production process according to claim 1, wherein the reducing agent is sodium borohydride.

13. A production process according to claim 1, wherein the compound represented by formula (3) has a cis configuration.

14. A process for producing a compound represented by formula (3):

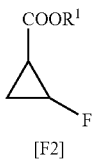

[F2]

wherein $R^1$ represents a C1-C8 alkyl group, a C6-C12 aryl group, a C2-C8 alkenyl group, or a C7-C26 aralkyl group, which process comprises reacting a compound represented by formula (1):

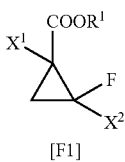

[F1]

wherein $X^1$ represents a hydrogen atom, a chlorine atom, a bromine atom, or an iodine atom;

$X^2$ represents a hydrogen atom, a chlorine atom, a bromine atom, or an iodine atom; when one of $X^1$ and $X^2$ is a chlorine atom, a bromine atom, or an iodine atom, the other is a hydrogen atom; i.e., $X^1$ and $X^2$ are not simultaneously hydrogen atoms; and $R^1$ has the same meaning as defined in formula (3)

with a reducing agent represented by formula (2):

 (2-1)

or

 (2-2)

wherein $M^1$ represents an alkali metal atom; $M^2$ represents an alkaline earth metal atom or a zinc atom; $R^2$ represents a hydrogen atom, a cyano group, a C1-C8 acyloxy group, or a C1-C6 alkoxy group; m represents an integer from 1 to 4; n represents an integer from 0 to 3; and the sum of m and n is 4, in the presence of one or more aprotic polar solvents selected from the group consisting of N,N-dimethylacetamide (DMAc), N-methyl-2-pyrrolidone (NMP), 1,3-dimethyl-2-imidazolidinone (DMI), and 1,3-dimethyl-3,4,5,6-tetrahydro-2(1H)-pyrimidinone (DMPU), and one or more Lewis acids selected from among halides and trifluoromethanesulfonic acid salts (triflates) of an atom selected from the group consisting of boron, magnesium, aluminum, silicon, scandium, titanium, chromium, manganese, iron, cobalt, nickel, copper, zinc, gallium, germanium, yttrium, zirconium, silver, cadmium, indium, tin, antimony, hafnium, lead, bismuth, lanthanum, cerium, and ytterbium.

15. A production process according to claim 14, wherein $X^1$ is a chlorine atom, a bromine atom, or an iodine atom, and $X^2$ is a hydrogen atom.

16. A production process according to claim 14, wherein $X^1$ is a hydrogen atom, and $X^2$ is a chlorine atom, a bromine atom, or an iodine atom.

17. A production process according to claim 14, wherein $X^1$ is a hydrogen atom, and $X^2$ is a chlorine atom.

18. A production process according to claim 14, wherein $X^1$ is a chlorine atom, and $X^2$ is a hydrogen atom.

19. A production process according to claim 14, wherein $R^1$ is a C1-C8 alkyl group.

20. A production process according to claim 19, wherein the C1-C8 alkyl group is a tert-butyl group.

21. A production process according to claim 14, wherein the aprotic solvent is an amide solvent or a cyclic urea solvent.

22. A production process according to claim 14, wherein the aprotic polar solvent is N,N-dimethylacetamide (DMAc).

23. A production process according to claim 14, wherein the Lewis acid is aluminum chloride, silane chloride, scandium chloride, chromium chloride, manganese chloride, iron(II or III) chloride, cobalt chloride, nickel chloride, copper(I or II) chloride, germanium chloride, zirconium chloride, silver chloride, indium chloride, tin(II) chloride, antimony(III) chloride, lead chloride, bismuth chloride, a boron trifluoride-ether complex, scandium triflate, copper triflate, silver triflate, tin triflate, or hafnium triflate.

24. A production process according to claim 14, wherein the Lewis acid is aluminum chloride, iron(II) chloride, cobalt chloride, lead chloride, silver chloride, or indium chloride.

25. A production process according to claim 14, wherein the reducing agent is sodium borohydride.

26. A production process according to claim 14, wherein the compound represented by formula (3) has a cis configuration.

* * * * *